(12) United States Patent
Cross et al.

(10) Patent No.: US 8,315,687 B2
(45) Date of Patent: Nov. 20, 2012

(54) HANDHELD, REPOSITIONABLE ECG DETECTOR

(75) Inventors: Brett Cross, Seattle, WA (US); Shannon Fong, Seattle, WA (US); Stacy E. Gehman, Seattle, WA (US); Kim J. Hansen, Renton, WA (US); Earl C. Herleikson, Cinebar, WA (US); Steven C. Hugh, Bellevue, WA (US); Thomas D. Lyster, Bothell, WA (US); Thomas A. Solosko, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 702 days.

(21) Appl. No.: 12/517,228

(22) PCT Filed: Nov. 30, 2007

(86) PCT No.: PCT/IB2007/054879
§ 371 (c)(1),
(2), (4) Date: Jun. 2, 2009

(87) PCT Pub. No.: WO2008/068695
PCT Pub. Date: Jun. 12, 2008

(65) Prior Publication Data
US 2010/0081913 A1   Apr. 1, 2010

Related U.S. Application Data

(60) Provisional application No. 60/869,009, filed on Dec. 7, 2006.

(51) Int. Cl.
*A61B 5/0404* (2006.01)

(52) U.S. Cl. .................. 600/392; 600/391; 600/509

(58) Field of Classification Search .................. 600/372, 600/382, 391–393, 509
See application file for complete search history.

(56) References Cited

U.S. PATENT DOCUMENTS

| 4,082,086 | A | * | 4/1978 | Page et al. ..................... 600/391 |
| 4,779,630 | A | * | 10/1988 | Scharnberg et al. .......... 607/142 |
| 5,042,481 | A | | 8/1991 | Suzuki et al. |
| 5,224,479 | A | | 7/1993 | Sekine |
| 5,343,869 | A | | 9/1994 | Pross et al. |
| 5,458,124 | A | | 10/1995 | Stanko et al. |
| 5,622,168 | A | | 4/1997 | Keusch et al. |
| 5,645,063 | A | | 7/1997 | Straka |
| 5,921,925 | A | * | 7/1999 | Cartmell et al. .............. 600/391 |
| 6,115,638 | A | * | 9/2000 | Groenke ........................ 607/142 |
| 6,161,036 | A | * | 12/2000 | Matsumura et al. .......... 600/509 |
| 6,453,186 | B1 | | 9/2002 | Lovejoy et al. |
| 6,572,636 | B1 | | 6/2003 | Hagen et al. |

(Continued)

FOREIGN PATENT DOCUMENTS

EP        1095612 A1   5/2001

(Continued)

*Primary Examiner* — Lee S Cohen
*Assistant Examiner* — Erin M Cardinal
(74) *Attorney, Agent, or Firm* — W. Brinton Yorks, Jr.

(57) ABSTRACT

An ECG monitoring device comprises an integral handheld device including a ECG electronic module and an electrode patch having a plurality of electrodes which contact a subject by conductive hydrogel. A release liner covers and protects the hydrogel prior to use and is removed to expose the hydrogel. A second release liner is removed to expose a pressure sensitive adhesive by means of which the device is attached to a subject. The first and second release liners may be parts of a single release liner layer. After use the electrode patch is disposable and the ECG electronic module is detached from the patch for reuse.

9 Claims, 8 Drawing Sheets

U.S. PATENT DOCUMENTS

| | | |
|---|---|---|
| 6,585,707 B2 * | 7/2003 | Cabiri et al. .................. 604/307 |
| 6,730,025 B1 | 5/2004 | Platt |
| 2002/0099277 A1 * | 7/2002 | Harry et al. .................. 600/301 |
| 2003/0055478 A1 * | 3/2003 | Lyster et al. .................. 607/142 |
| 2003/0069510 A1 | 4/2003 | Semler |
| 2003/0073915 A1 | 4/2003 | McLeod et al. |
| 2005/0154325 A1 | 7/2005 | Lauter et al. |
| 2006/0224072 A1 | 10/2006 | Shennib |
| 2008/0139953 A1 * | 6/2008 | Baker et al. .................. 600/509 |
| 2008/0275327 A1 * | 11/2008 | Faarbaek et al. .............. 600/382 |

FOREIGN PATENT DOCUMENTS

| | | |
|---|---|---|
| GB | 2368799 A | 5/2002 |
| WO | 0222010 A | 3/2002 |

* cited by examiner

HANDHELD, REPOSITIONABLE ECG DETECTOR

This invention relates to handheld devices for performing medical diagnosis and, in particular, to a handheld device which can be repositioned on the body to detect and/or record an ECG waveform.

During the course of many patient examinations there is often a need to quickly ascertain the condition of the patient by measuring certain patient parameters such as blood pressure, temperature, blood oxygenation level, blood glucose levels, and cardiac function. Devices are available which enable medical practitioners to quickly measure a patient's blood pressure, temperature and blood glucose levels. The device currently used for quick cardiac function monitoring is the stethoscope. If the physician wishes to view a patient's heart rhythm or ECG (electrocardiogram), time is then spent attaching five to twelve electrodes to the patient's chest, arms and legs, connecting each lead to a wire, and recording, downloading and finally viewing the ECG. This method is time consuming and presents numerous difficulties.

One challenge is chest hair. Men often have chest hair and most electrodes do not stick well over hair. Electrodes tend to have poor and faulty connections unless additional time is taken to carefully shave the patient's chest in several places in order to prepare the skin for good electrode connections. Shaving may also be uncomfortable for the patient, both during the office visit and in subsequent days as the hair regrows. In addition, shaving and skin preparation needs to occur virtually every time a physician desires to monitor the patient's ECG waveform. Since shaving and skin preparation requires time and the time available with each patient is short, physicians may opt to forgo ECG monitoring on some patients when it is not absolutely necessary, even though good practice might suggest otherwise.

In addition to the sub-optimal electrode connections caused by body hair, lead wires pulling on the electrodes cause additional problems. The typical ECG lead wires are relatively heavy and the torque that they apply to the electrodes tends to cause the electrodes to peel away from the skin. Even a partially loose electrode can cause noise in the ECG system.

ECG electrode placement presents challenges to women as well. Although women may not need to shave prior to an ECG exam, they may be required to remove layers of clothing in order to allow electrode and lead wire attachment to several locations across the chest. This is not only time consuming, but cold and uncomfortable and potentially embarrassing.

Another challenge with the separate electrode ECG system is that in order to compare subsequent ECG recordings to a baseline, it is desirable to place the electrodes at the same locations on the body each time a measurement is made. With five to twelve independent electrodes, putting the electrodes in exactly the same location during each examination is difficult.

Post-operative patients also present a challenge to quick ECG measurements. The chest areas of post-operative patients are often covered with tubes, bandages and leadwires from other devices. It can be difficult to find areas of the body to attach extra electrodes and lead wires in order to obtain an ECG measurement.

In addition to physician office visits, there can be other times when the physician would like the patient to independently measure and record his or her own cardiac parameters at home and communicate them to the physician's office on a regular basis. Devices are available which enable independent patient blood pressure, temperature and blood glucose monitoring, and the primary device for home ECG monitoring is the Holter monitor. Holter devices and event recorders are available to measure and record an ECG signal for twenty-four hours to several weeks, but these device must be worn continuously while they are in use. There is no device currently available which allows the patient to independently take an ECG for 30 seconds or a minute at a time, and then put the device away until the next measurement time. Furthermore, there are often times when a patient may begin to feel a heart event, such as a skipped beats or palpitations. Unless he or she is already wearing a Holter monitor or event recorder, it may take too long to attach a standard electrode set and record the cardiac signal during the event. By the time the patient attaches the electrodes of the monitor, the arrhythmia may have ended.

Accordingly it is desirable for an ECG measurement and recording device to be able to address these and other shortcomings of prior art devices.

In accordance with the principles of the present invention, an ECG monitoring device is provided with electrodes located close to the monitoring unit without the conventional electrode leads. The ECG monitoring device may be attached to the patient for ECG recording by conductive adhesive covering the electrodes. Prior to attachment to the patient, the monitoring device may be pressed against the patient to locate a good site for ECG measurements or to quickly monitor the ECG. The monitoring device may be repositioned at this time until a good measuring site is found. When this process is finished the ECG monitoring device may be set aside until needed for a subsequent patient, or attached to the patient for ECG monitoring over an extended period of time. The small, portable size of the monitoring device, and the ability to mark a placement location on the patient, enable the patient to use the monitoring device for quick and reliable ECG measurement or recording at home.

In the drawings:

FIG. 2b is a functional block diagram of the ECG monitoring device of FIG. 2a.

Figure 1:
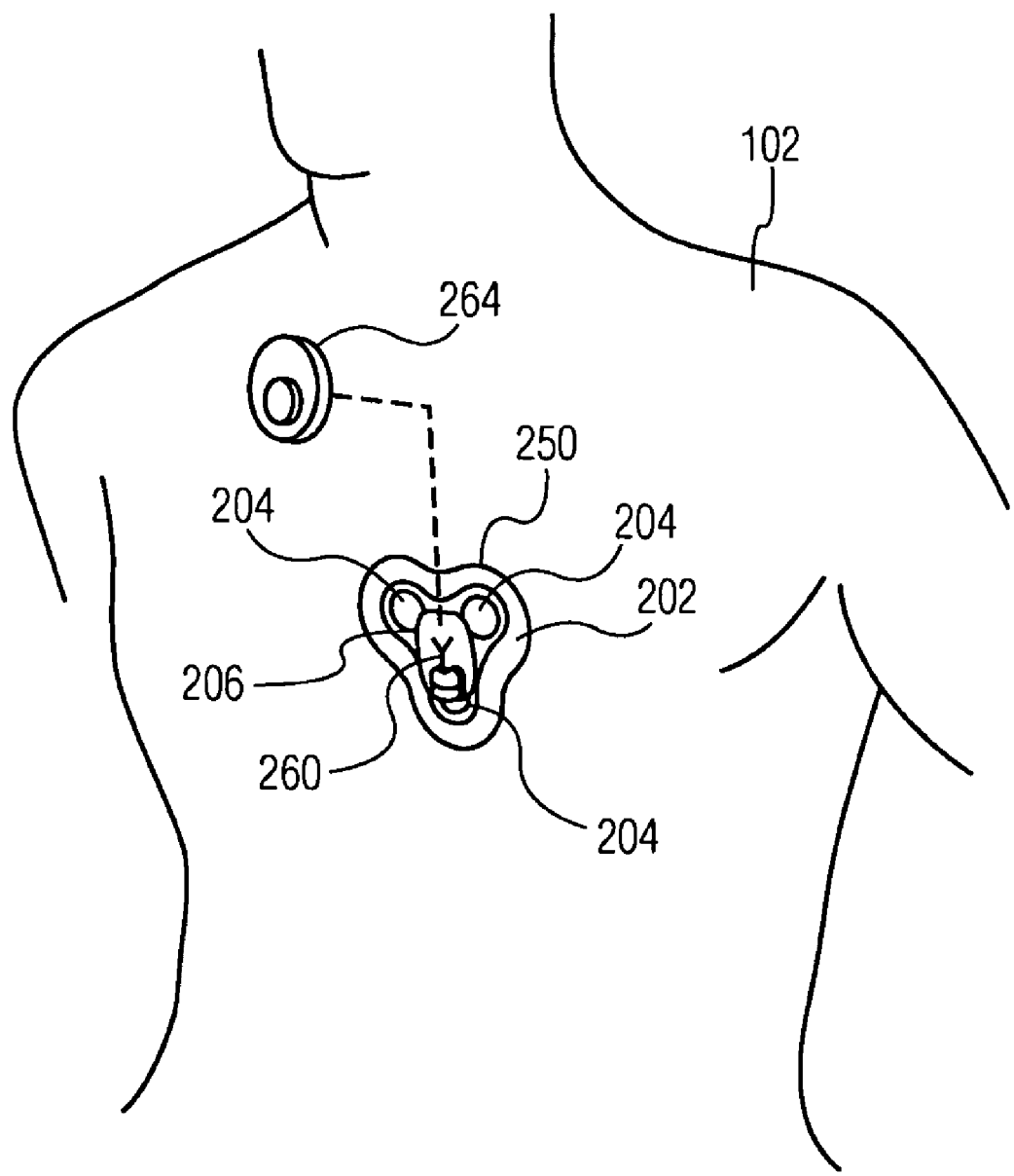
FIG. 1 illustrates a patient with an ECG monitoring device of the present invention attached to the chest of the patient.

Referring first to FIG. 1, a patient 102 is shown wearing an ECG monitoring device 250 of the present invention. The ECG monitoring device 250 includes a plurality of electrodes 204 and can be adhesively attached to the patient 102 by a retention seal 202. The ECG monitoring device 250 includes a holster or clip 260 that can be used to removably attach a miniature monitor/recorder device 264. The clip 260 is formed with conductive traces 206 that are connected to the miniature monitor/recorder device 264 when it is clipped into place, thereby allowing electrical signals detected by the electrodes 204 to be coupled to the monitor/recorder device 264. As is apparent from the drawing, the ECG monitoring device 250 is relatively compact and does not have a plurality of wires extending across the torso of the patient 102. Additionally, having a miniature monitor/recorder device 264 clipped to the ECG monitoring device 250 provides a compact medical monitor/recorder system 264 that can be readily worn by the patient 102 on a small area of the body and avoids many of the difficulties posed by conventional monitor/recorder systems and electrode configurations.

Figure 2A:
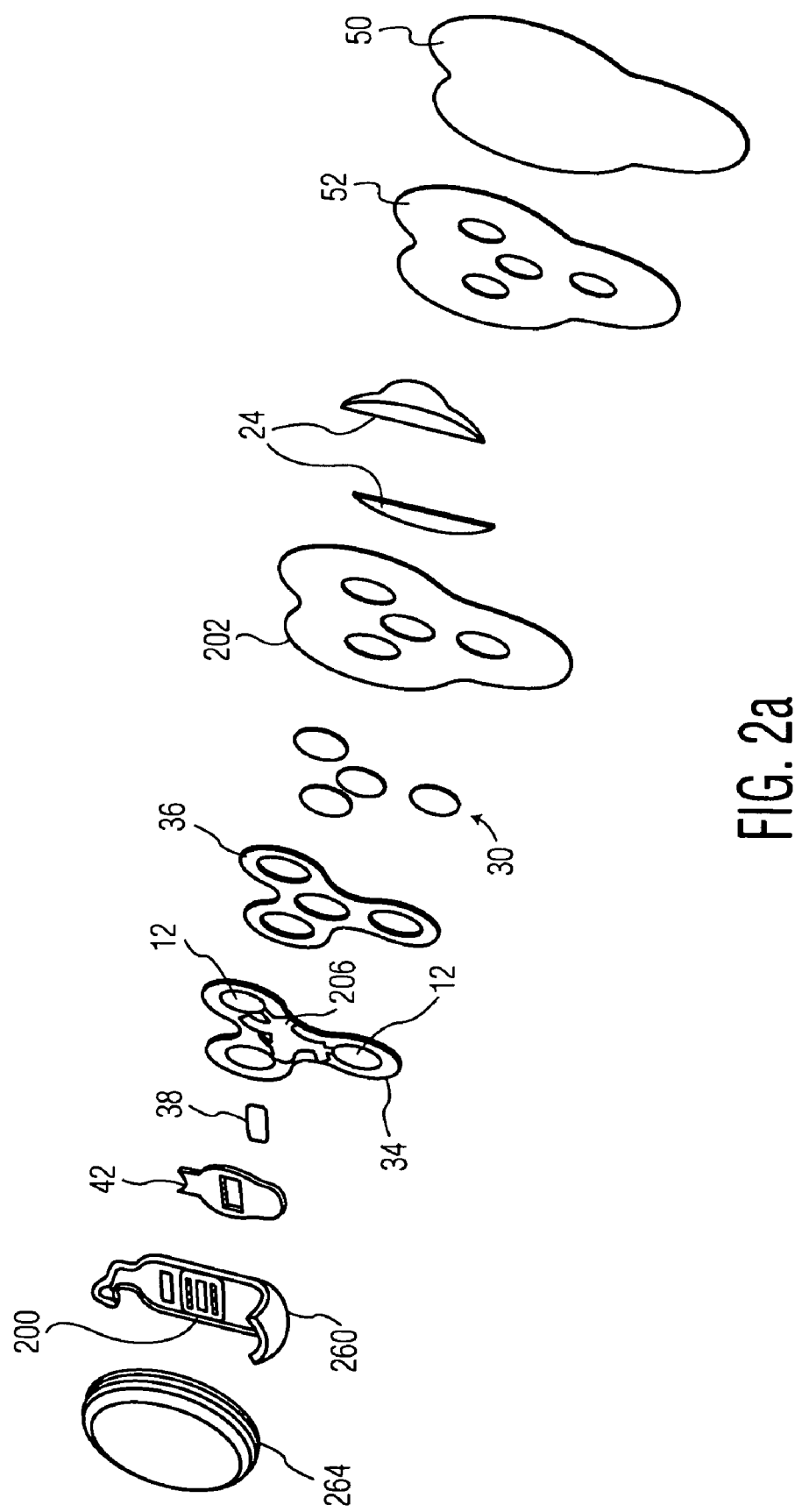
FIG. 2a is an exploded view of a first ECG monitoring device constructed in accordance with the principles of the present invention.

FIG. 2a is an exploded view of the electrode patch and monitor/recorder module of an ECG monitoring device of the present invention. The monitor/recorder module 264 is shown on the left side of the drawing and can clip into the holster 260. The back of the monitor/recorder module has a connector or contacts such as the conductive silicone contacts shown in this example which engage a mating connector or contacts on the holster 260. On the back of the holster 260 is a layer of medical grade pressure sensitive adhesive 42 which attaches the holster to an electrode circuit layer 34. The electrode circuit layer 34 in this example has four metallic circular electrodes formed on it and has printed silver or carbon contacts on the side facing the holster which electrically engage the contacts or connector on the holster by means of conductive pressure sensitive adhesive 38. The conductive adhesive 38 in this example is peripherally sealed from the environment by the pressure sensitive adhesive layer 42.

A foam frame 36 overlays the electrode circuit layer 34 and has three circular openings which are aligned with the electrodes of the electrode circuit layer. The frame 36 holds individual pieces 30 of hydrogel and also serves to provide a dielectric barrier laterally between the electrodes. The frame 36 may be slightly thinner than the disks of hydrogel so that the hydrogel will extend slightly beyond the surface of the retention layer 202 and into good contact with the skin of the patient. The retention seal is a thin, flexible layer such as 1-mil polyurethane which is coated on the skin-facing side with medical grade pressure sensitive adhesive. The back of the retention seal is adhesively attached to the foam frame 36 to retain the hydrogel disks 30 in place. The holes in the retention seal 202 are slightly smaller than the hydrogel disks. The adhesive on the retention seal 202 holds the patch to the skin of the patient and provides a barrier against moisture passage from the patient.

Two handling tabs 24 extend from the sides of the retention seal and are used to hold the patch while applying the patch to the skin. Generally the tabs are removed after the patch has been adhesively attached to the patient.

An inner release liner 52 covers the retention seal and must be removed in order to adhesively attach the patch to the patient. The inner release liner has a hole through which each piece of electrode hydrogel 30 can extend. The inner release liner 52 is covered by an outer release liner 50 which, like the inner release liner, is made of paper or film and can be rigid or flexible. The outer release liner contacts the hydrogel and protects the hydrogel from contamination prior to use and helps prevent moisture loss from the hydrogel.

In accordance with the principles of the present invention, the two release liners provide the ECG monitoring device with several modes of use. First, with the outer release liner 50 in place, the patch is protected prior to use. When the outer release liner is removed, the hydrogel is exposed through the holes in the inner release liner. The ECG monitoring device can now be held against the skin of the patient to acquire an ECG signal and can be repositioned as desired. Once an appropriate location is found for attachment of the unit, a location on the body where a clear ECG signal is received, the inner release liner is peeled away and the patch attached in place by the pressure sensitive adhesive of the retention seal 202. This is illustrated by the functional block diagram of FIG. 2b, which shows conductive hydrogel 30 making direct contact with the skin 20 in two or more locations. The hydrogel improves the electrical conductivity between a silver/silver chloride (Ag/AgCl) electrode layer 12 and the skin. Typical components of a conductive hydrogel include water (which acts as the solvent), water-soluble monomers which crosslink to give structure to the gel and which may also provide skin adhesion, humectant materials which reduce the dryout characteristics of the hydrogel, and electrolytes or salts such as sodium chloride or potassium chloride dissolved in water, which provide the ionic conductivity. One advantage of hydrogels over other conductive electrolytes is that they can be removed cleanly from the skin without leaving a residue. The silver/silver chloride electrode layer contacts the hydrogel on one side, and silver or copper traces 206 on the other side. The electrode layer 12 is the interface at which ionic conduction through the hydrogel changes to electronic conduction to the monitor/recorder device 264. The traces, which may be printed or etched, provide electrical connection between the electrode and the monitoring device via an electro-mechanical connector 200 which, in the example of FIG. 2a, is shown on the holster 260. The traces may also be printed Ag/AgCl which is electrically conductive due to the silver particles it contains.

Figure 2B:
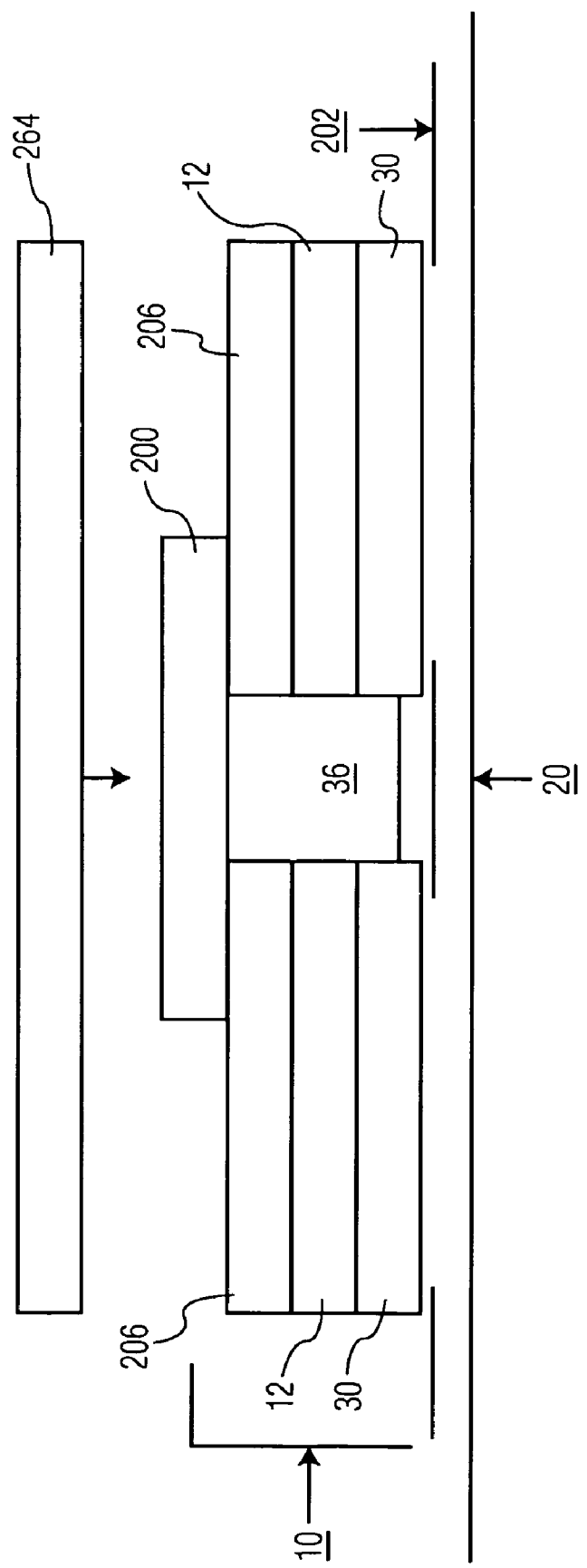

The purpose of placing the electrodes in contact with the skin is to measure the voltage difference between two or more electrodes. To this end, the reusable monitor/recorder device 264 is attached to the electro-mechanical connector 200. This device is typically a high impedance device which provides an effectively open circuit between electrodes and prevents current from flowing between them. The diagram of FIG. 2b shows the multiple electrodes that make contact with the skin. Each electrode is composed of the Ag/AgCl layer 12 and the hydrogel layer 30 which contacts the skin. To separate the electrodes and ensure they don't touch each other, a dielectric or barrier material is needed to fill in the gaps between each electrode. This function is provided by the foam frame 36 in the example of FIG. 2a. A thin, flexible, retention layer 202 is used to hold the separate hydrogel pieces firmly in the patch 10. Since hydrogels can be formulated to exhibit adhesive properties, the hydrogel disks may stick to the skin and peel out of the patch as the patch is moved from place to place unless they are held in place by the retention seal 202. In the patch design (Ag/AgCl) retention seal overlaps the hydrogel edges, keeping the individual pieces anchored in the patch.

Advantages of an embodiment of the present invention such as the previous example can be numerous, depending upon the particular implementation. First, when physicians prescribe an extended wear, short-vector ECG monitoring device such as the one described above, they often need to determine the acceptable and optimal locations where this patch and device should be worn. Optimal locations will vary between patients. Depending on the physical characteristic which the physician wants to monitor, optimal locations can be defined as those which capture p-waves, those which offer the largest or clearest QRS amplitude, or those with the highest ECG-signal to muscle-noise ratio. An ECG monitoring device of the present invention allows clinicians to determine the optimal patch and monitor locations. The device is a small, handheld, repositionable device which allows the physicians to query several locations and decide which ones to monitor prior to adhesively attaching the device to a particular body location.

Second, an ECG monitoring device of the present invention can reduce the time it takes a physician or nurse to capture, view and record a patient's ECG waveform. The steps to do this are simple. A disposable multi-electrode patch is removed from a sealed pouch and snapped to the battery-powered monitor module. Once the outer release liner 50 is removed from the patch 10, the physician holds the ECG monitoring device in one hand and presses it on the chest so that the electrodes 12,30 make good contact with the skin. Shaving is generally not required since the physician is holding the device and pushing it gently into the skin causing the hydrogel to work its way through the hair and make contact with the skin.

Upon sensing patient contact and turned on, the monitor begins capturing and recording the patient's ECG. At the same time, it may also or alternatively display the ECG waveform on a small screen, or send the ECG data either by wire or wirelessly (i.e., via Bluetooth technology) to a hand-held device or computer where it may be instantly seen, reviewed, and annotated if desired. Another benefit of the instant ECG display is that the physician can see real time ECG and instantly note the effects of exercise, position, medication, etc. on the patient's ECG waveform.

Since the device is hand held with the lubricating hydrogel in contact with the skin, the physician can reposition the device a number of times to capture the ECG signal in different device orientations, or on different areas of the chest or other locations on the body. In some embodiments, the only adhesive material touching the skin is the hydrogel which is far less adhesive than the pressure-sensitive adhesive layer 202 which is still covered by the inner release layer 52 at this time. In other embodiments the hydrogel is solid and does not adhere to the skin at all. Alternatively the gel can be a wet gel, also without adhesive properties. This ability to reposition the device on the skin allows the clinician to find the electrode placement that best captures the desired ECG waveform such as P waves. This also allows the physician to check the patient intermittently during or after exercise if desired. When the hydrogel is self-adhesive, the ECG-scope may be positioned, pressed down firmly, and then left untouched in place for as long as the physician requires, with the adhesive hydrogel holding the device to the skin. With an appropriately adhesive hydrogel, no pressure sensitive adhesive may be necessary for attachment of the device to the patient.

Since the ECG module and the electrode patch are small, the device may be used to capture the ECG on the highly-cluttered chests of post-operative patients. The small size allows the device to be positioned between leadwires, sutures, bandages and other electrodes and devices. Also because of its small size, patients may not be required to remove any clothing in order to obtain an acceptable ECG. The small device can be placed under clothing or require only minimal unbuttoning to enable placement in desired locations.

With integrated electrodes and no lead wires, an ECG monitoring device of the present invention does not place a torque on the individual electrodes which might cause them to peel partially or fully off the skin. Since it is small and handheld, the physician can press the device more or less firmly against the skin as required. The real time ECG display can guide the clinician to determine optimal location, orientation and force.

When a physician instructs a patient to capture ECG data regularly at home, an ECG monitoring device of the present invention can allow the patient to quickly and easily press the device to the skin in the desired location, record the ECG data, and then send it via cell phone, Internet, fax or other communication medium to the physician's office. Since the electrode patch is small and self-contained, the physician can mark the exact patch location on the skin while the patient is in the physician's office, enabling the patient or nurse to place the patch in the same location for each subsequent measurement. This ensures that any changes seen between baseline and subsequent ECG readings are real and not due to differences in electrode location. This ease of use enables a patient to quickly capture an ECG at times when he or she feels the onset of irregular cardiac activity.

The multi-vector ECG of the device described above will usually provide higher quality ECG data as compared to single vector bipolar devices.

Figure 3:
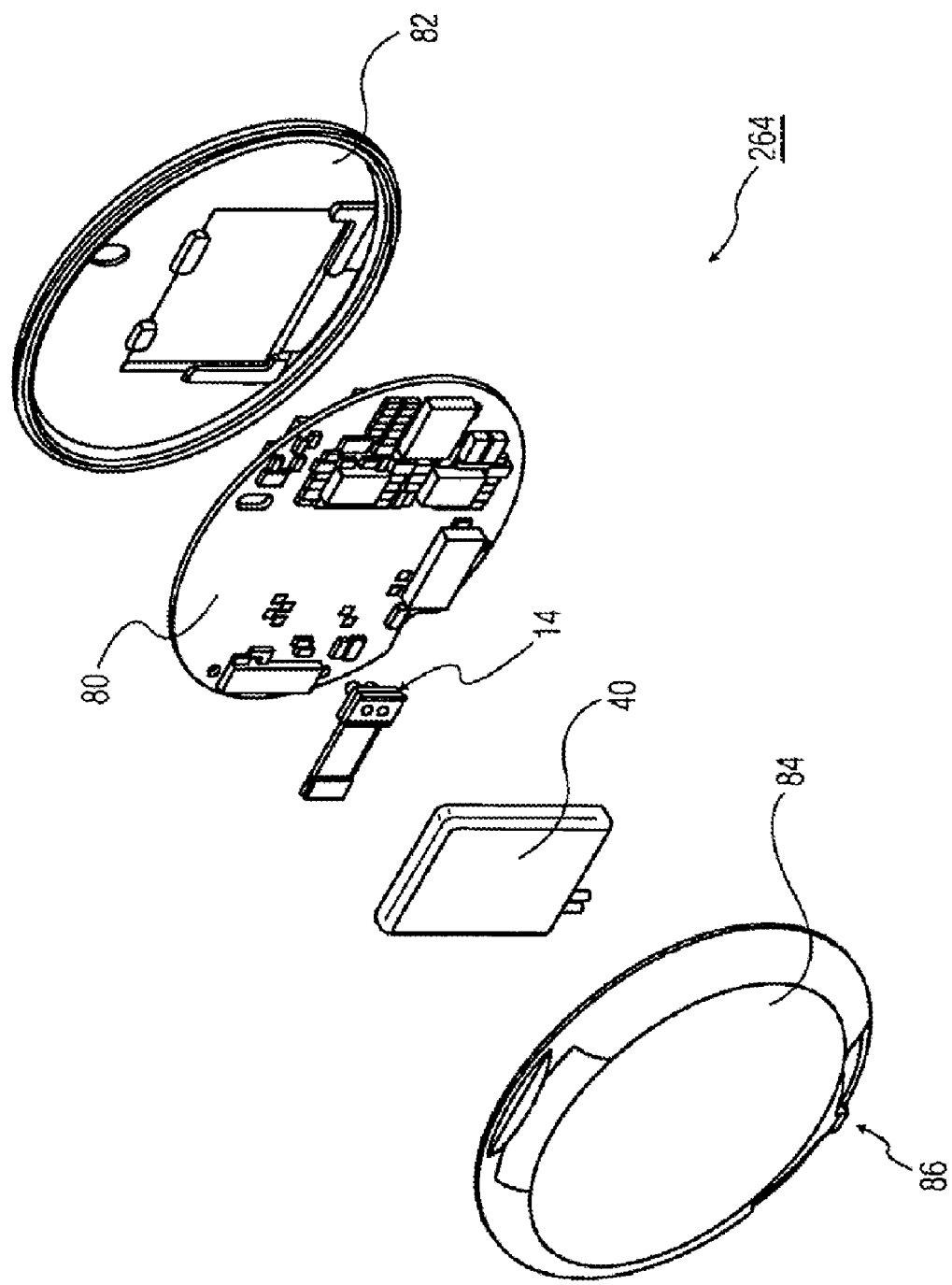
FIG. 3 is an exploded view of the electronics module of the ECG device of FIG. 2.

FIG. 3 shows an exploded view of the monitor/recorder module 264 of FIG. 2. The electronics module 264 has a clamshell case of two halves 82 and 84. On the lower edge of the case half 82 is a connector 86 that connects to a mating connector 200 of the holster 260. The electrical components of the device are located on a printed circuit assembly 80, including in this example a piezoelectric motion sensor 14 as described in U.S. patent application 60/748,916, filed Dec. 8, 2005 which is incorporated herein by reference. A battery 40 is located between the printed circuit assembly and the case half 84 to power the module.

Figure 4A:
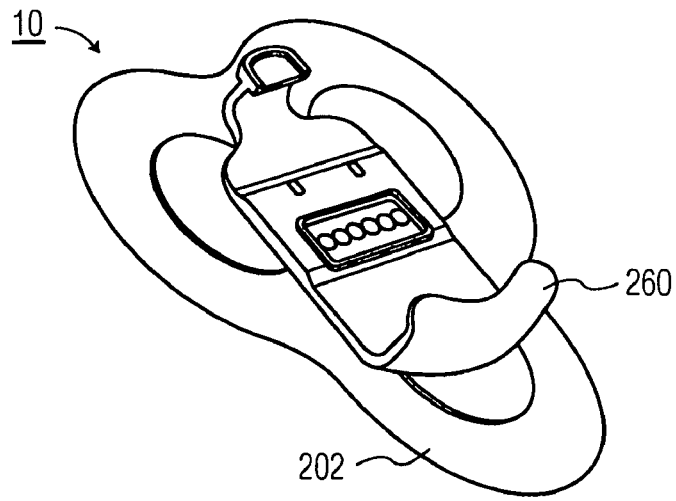
FIGS. 4a and 4b illustrate an ECG monitoring device of the present invention and its disposable electrode patch.
Figure 4B:
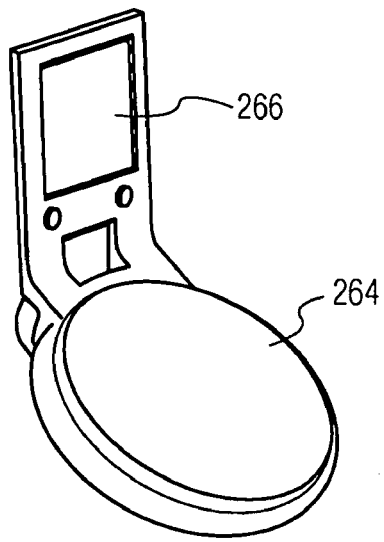

FIGS. 4a and 4b provide perspective views of an ECG monitoring device constructed in accordance with the principles of the present invention. The electrode patch 10 is shown in FIG. 4a with the module holster 260 facing outward. The monitor/recorder module 264, shown in FIG. 4b, clips into the holster 260 and is thereby connected to the electrodes of the patch 10. In this example the module 264 has an integrated LCD display 266 which is hinged to fold down against the module body when the device is worn by the patient. If the physician want to take a quick look at the patient's ECG waveform, the display 266 can be flipped up to the position shown in FIG. 4b and the physician can observe the ECG waveform on the display while the patient continues to wear the patch and monitoring module.

Figure 5:
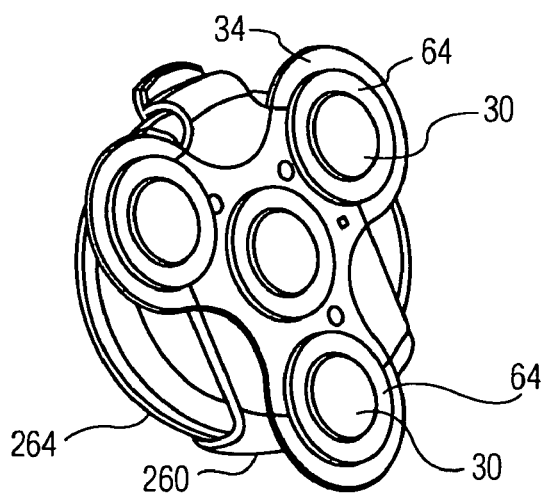
FIG. 5 illustrates another example of an ECG monitoring device of the present invention and its disposable electrode patch.

FIG. 5 illustrates an ECG monitoring device of the present invention with disposable hydrogel over reusable electrodes. The electronics module 264, holster 260 and electrode layer 34 can be a unitary assembly in this implementation, or can support a removable electronics module 264 as in the previous examples. The conductive electrode areas on the electrode layer 34 may be printed Ag/AgCl ink as before, but as ink may not last through repeated cleaning and disinfecting, the electrodes may be plated metal snaps or metal disks held in place by the electrode layer. The electrodes may alternatively be made of conductive silicone that is either over-molded onto the holster 260 or directly over contacts of the module 264.

An ionic conductor is then applied over the electrode areas just prior to use of the device. The ionic conductor may be a conductive paste or solution, but preferably are hydrogel disks that attach to the electrodes. Suitable disks for this purpose can be formed of a thin substrate such as 3-mil polyester which is conductive on both sides by a covering of conductive ink. Through-hole connections electrically interconnect both sides. The side opposing the electrode of the device is coated with a conductive pressure sensitive adhesive which will attach and electrically connect the disk to an electrode. On the outward (body-facing) side of the substrate is a disk of conductive hydrogel 30 which is surrounded by a foam ring 64 to insulate the hydrogel from neighboring electrodes. In use, the hydrogel disks are removed from an airtight container and one is adhesively attached to each electrode. After use the hydrogel disks are peeled off of the electrode areas of the electrode layer and disposed of properly. The device is cleaned and sterilized in preparation for another use.

Figure 6:
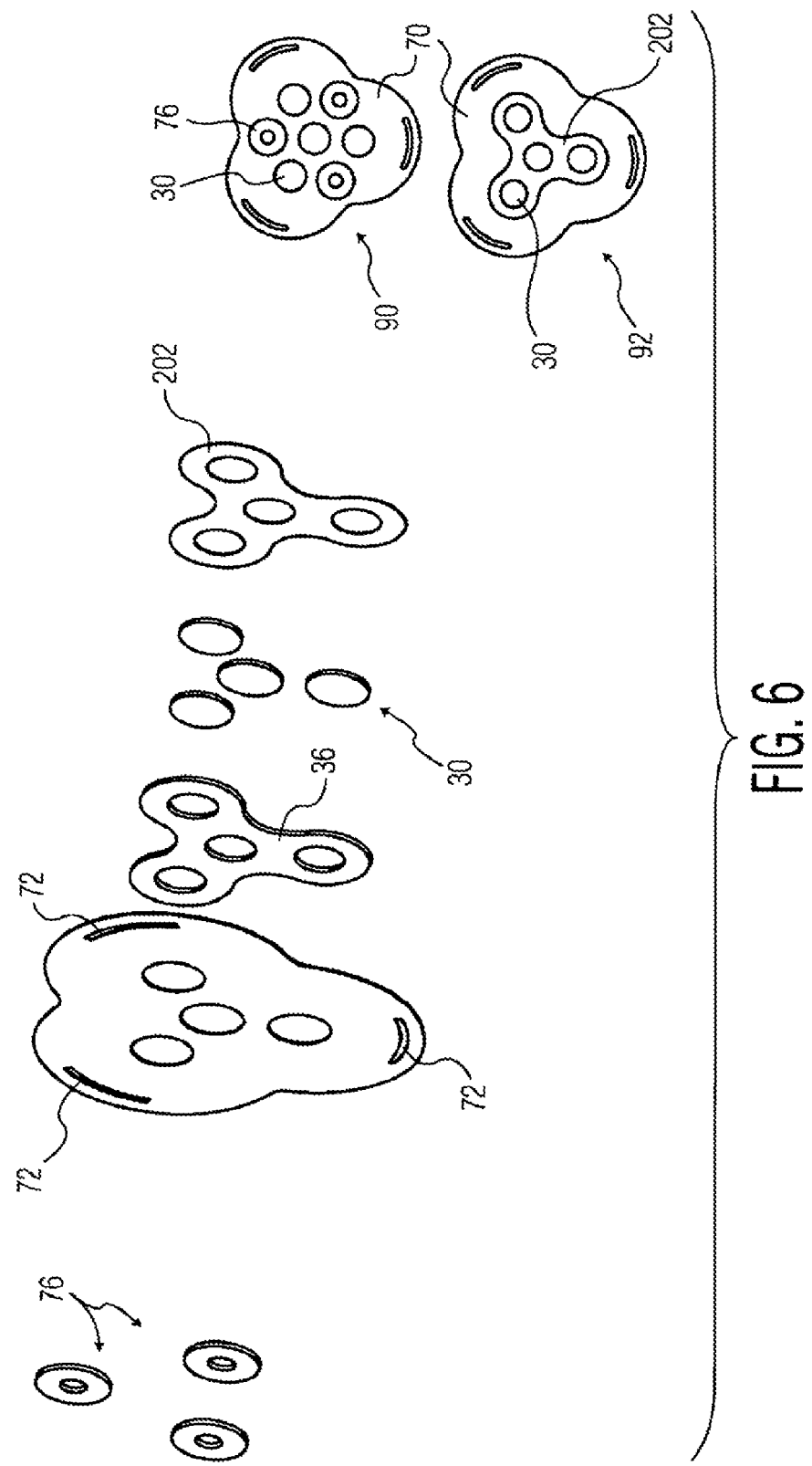
FIG. 6 is an exploded view of another example of an electrode patch for an implementation of the present invention.

FIG. 6 illustrates another example of a patch for an ECG monitoring device of the present invention. This example provides a means to aid in marking the placement of the patch on the body. A substrate 70 has three openings 72 around its periphery. When the patch is positioned on the patient, marks can be made through these openings, to which the patient can align the patch for proper attachment at home or at a subsequent examination. The substrate 70 has holes through it for the electrodes. An insulating frame 36 is aligned with these holes. Hydrogel disks 30 are placed in each hole of the insulating frame 36 and are held in place by an overlaying retention seal 202. Foam locator rings 76 can also be positioned on the patient-facing side of the substrate 70 to aid in placement. The assembled patch is shown in a plan view from the back (module-connecting side) at 92, and in a plan view of the patient-facing side at 90.

Figure 7:
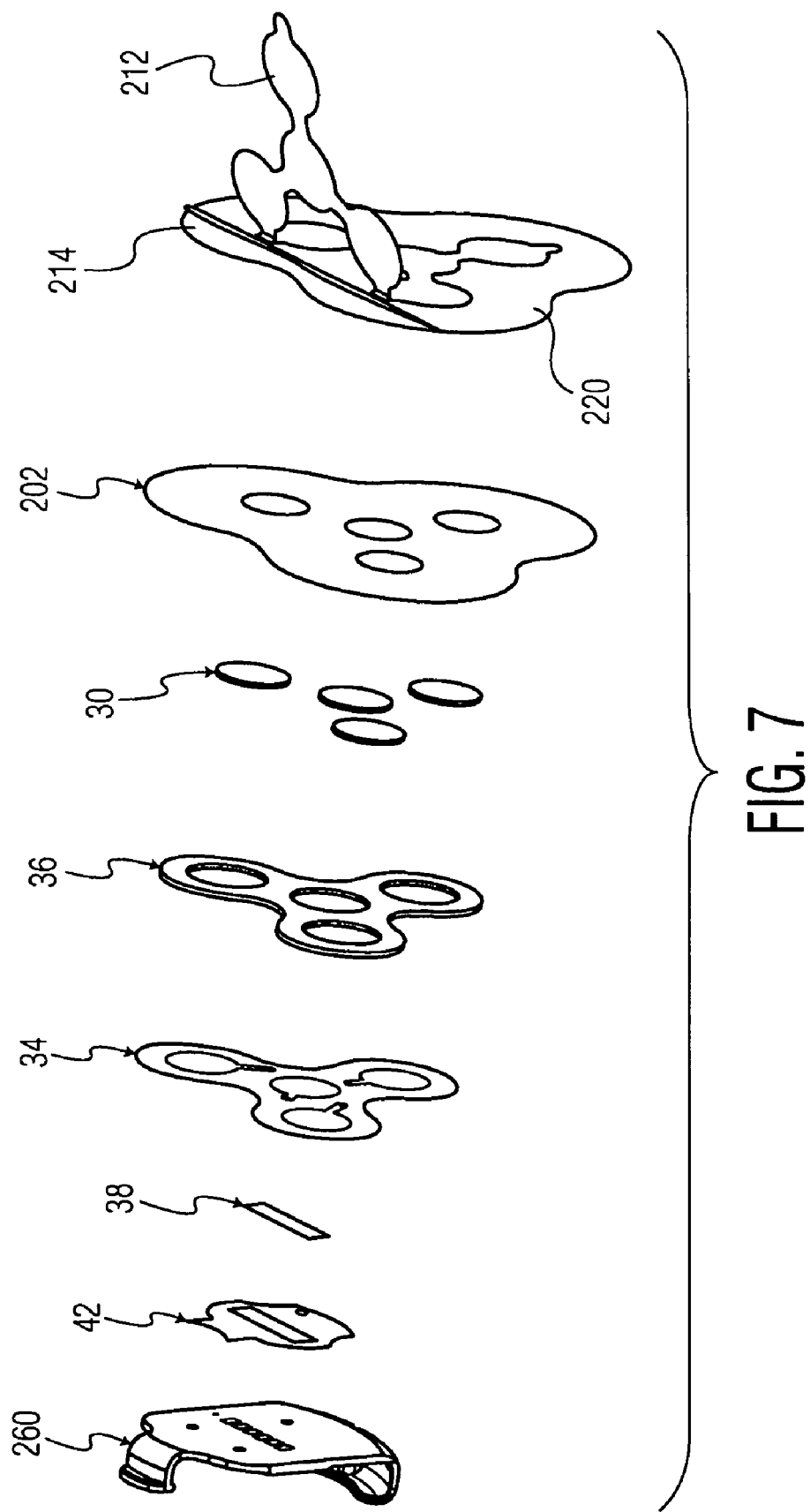
FIG. 7 is an exploded view of another example of an electrode patch for an implementation of the present invention which has an electrode release liner that can be easily removed.

FIG. 7 illustrates another example of an ECG monitor patch of the present invention in an exploded view in which the same reference numerals as FIG. 2a are used for the same elements. This example uses a single release liner over the retention layer 202. A portion 212 of the release liner 220 which covers the electrode areas is perforated so as to peel away and upward from the main portion of the release liner 220, revealing the electrode hydrogel for a survey exam of possible attachment locations where a suitable ECG signal can be detected. Once a suitable location on the body has been found, the user grasps a tab 214 at the top of the release liner 220 and peels the entire release liner off of the retention layer 202 so that the patch can be adhesively attached to the body.

Figure 8:
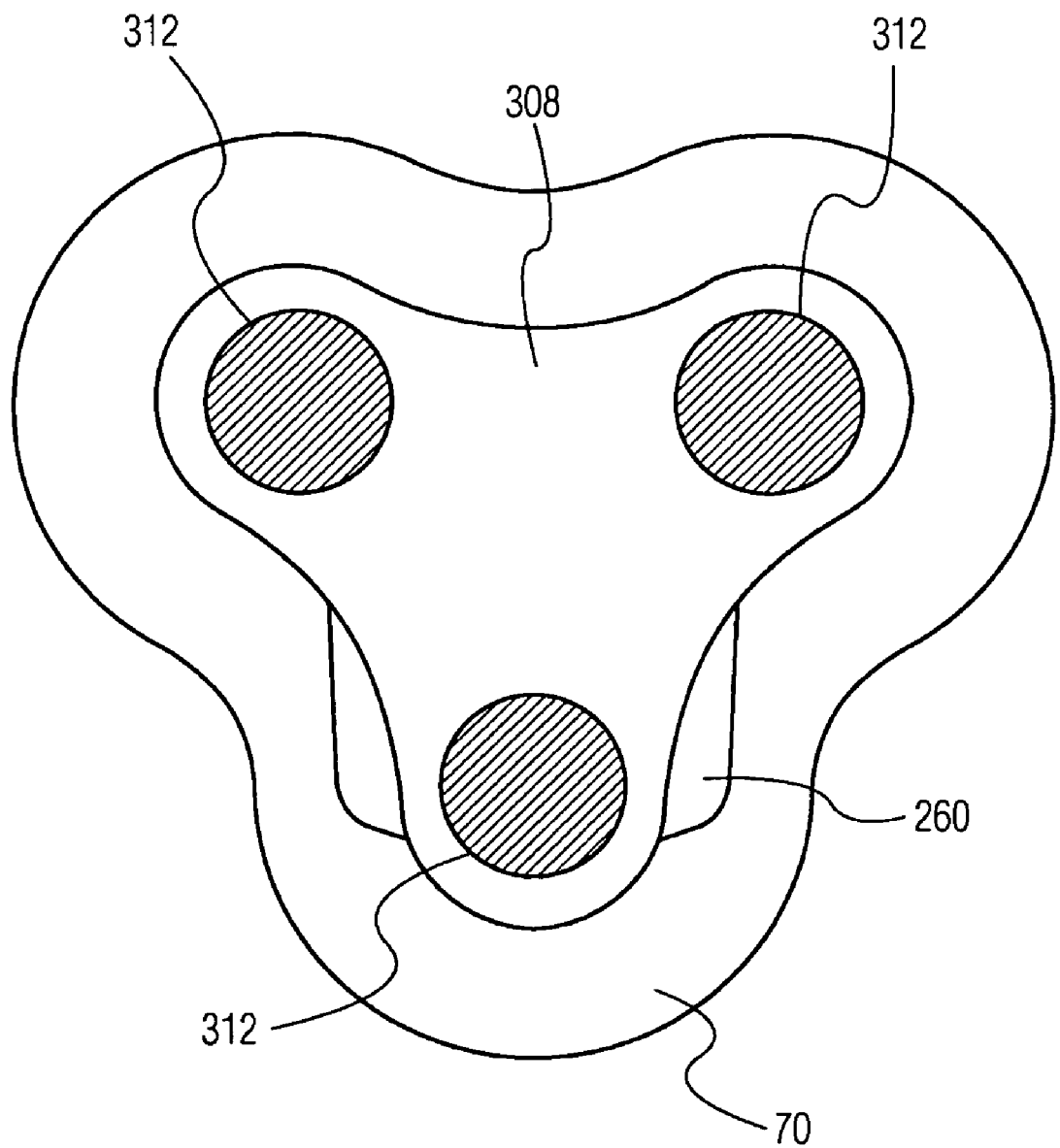
FIG. 8 is a plan view of an electrode patch constructed in accordance with the principles of the present invention and which can be used with the release liner in place.

FIG. 8 illustrates another example in which the ECG monitor can be used for a patient survey prior to the removal of any release liner portion. In this example the electrode hydrogel and the pressure sensitive adhesive of the retention seal, when used, are covered by a release liner 308. The release liner 308 has areas 312 aligned with the covered electrodes which are formed of an embedded conductive material such as metallic foil. The balance of the release liner 308 is made of a nonconductive material such as Kraft paper or a polymeric film. The areas 312, which may be augmented with gel, provide conduction paths by which the ECG signal can be detected by the ECG monitoring device prior to any release liner removal. The physician can slide the ECG monitoring device over the body, looking for an appropriate attachment site or simply to take a quick look at the patient's ECG waveform. When an appropriate attachment site has been found the release liner 308 is peeled away and the ECG monitoring device attached to the patient at the located site. Alternatively, after surveying the patient's ECG, the physician can put the unit away with the release liner 308 intact and suitable for use at another time.

What is claimed is:

1. An ECG monitoring device disposed to be worn on a subject body comprising:
   a handheld electrode patch including a plurality of electrodes configured to make contact with the subject body by separate, electrically conductive areas of hydrogel;
   a removable release liner covering the areas of hydrogel prior to use; and
   an ECG electronic module which attaches to the electrode patch in electrical communication with the electrodes,
   wherein the removable release liner further comprises a sheet of nonconductive material having conductive areas aligned with the areas of hydrogel.

2. The ECG monitoring device of claim 1, wherein the electrode patch is disposable and the ECG electronic module is reusable after use.

3. The ECG monitoring device of claim 1, wherein the electrode patch further includes an alignment edge configured to align the electrode patch on the subject body.

4. The ECG monitoring device of claim 3, wherein the alignment edge is part of an alignment aperture of the electrode patch.

5. The ECG monitoring device of claim 1, wherein the ECG electronic module further includes a communication link adapted to transmit received ECG data to a storage and/or display device.

6. The ECG monitoring device of claim 1, wherein the ECG electronic module further includes a display adapted to display received ECG data.

7. A method for acquiring ECG data of a subject with a handheld device including an ECG electronic module and a plurality of electrodes having conductive hydrogel, the hydrogel covered with a release liner comprising a nonconductive layer having conductive areas aligned with the hydrogel, the method comprising:
   placing the release liner of the handheld device in contact with the subject to acquire ECG data;
   removing the release liner to expose the hydrogel; and
   placing the hydrogel in contact with the subject to acquire ECG data.

8. The method of claim 7, further comprising:
   marking the location of the electrode patch in relation to the subject.

9. The method of claim 7, wherein removing the release liner further comprises exposing a pressure sensitive adhesive; and attaching the handheld device to the subject by means of the pressure sensitive adhesive.

* * * * *